United States Patent [19]

Hanko et al.

[11] Patent Number: 5,364,942
[45] Date of Patent: Nov. 15, 1994

[54] SULPHONYLBENZYL-SUBSTITUTED IMIDAZOPYRIDINES

[75] Inventors: Rudolf Hanko, Duesseldorf; Jürgen Dressel, Wuppertal; Peter Fey, Wuppertal; Walter Hübsch, Wuppertal; Thomas Krämer, Wuppertal; Ulrich E. Müller, Wuppertal; Matthias Müller-Gliemann, Solingen-Ohligs; Martin Beuck, Erkrath; Stanislav Kazda; Claudia Hirth-Dietrich, both of Wuppertal; Andreas Knorr, Erkrath; Johannes-Peter Stasch, Wuppertal; Stefan Wohlfeil, Hilden; Özkan Yalkinoglu, Wuppertal, all of Germany

[73] Assignee: Bayer Aktiengesellschaft, Leverkusen, Germany

[21] Appl. No.: 18,964

[22] Filed: Feb. 18, 1993

[30] Foreign Application Priority Data

Feb. 27, 1992 [DE] Germany ............................. 4206042

[51] Int. Cl.$^5$ ................. C07D 471/04; C07D 471/06; A61K 31/415; A61K 31/44
[52] U.S. Cl. ....................................... 546/118; 546/14
[58] Field of Search ................... 546/14, 118; 514/303

[56] References Cited

FOREIGN PATENT DOCUMENTS

| | | |
|---|---|---|
| 0324377 | 7/1989 | European Pat. Off. . |
| 0403159 | 12/1990 | European Pat. Off. . |
| 0425211 | 5/1991 | European Pat. Off. . |
| 9009997 | 9/1990 | WIPO . |
| 0403158 | 12/1990 | WIPO . |
| 91/00281 | 1/1991 | WIPO . |
| 9203423 | 3/1992 | WIPO . |

OTHER PUBLICATIONS

Journal of Medicinal Chemistry, Bd. 35, Feb. 1992, Washington US, pp. 663–676, M. D. Varney et al., (vol. 35, No. 4).

Primary Examiner—C. Warren Ivy
Assistant Examiner—D. Margaret M. Mach
Attorney, Agent, or Firm—Sprung Horn Kramer & Woods

[57] ABSTRACT

Sulphonylbenzyl-substituted imidazopyridines can be prepared by reacting correspondingly substituted imidazopyridines with sulphonylbenzyl compounds. The sulphonylbenzyl-substituted imidazopyridines can be employed as active compounds in medicaments, in particular for the treatment of hypertension and atherosclerosis.

10 Claims, No Drawings

SULPHONYLBENZYL-SUBSTITUTED IMIDAZOPYRIDINES

The invention relates to sulphonylbenzyl-substituted imidazopyridines, a process for their preparation and their use in medicaments, in particular as antihypertensive and antiatherosclerotic agents.

It is known that renin, a proteolytic enzyme, splits off the decapeptide angiotensin I from angiotensinogen in vivo, the angiotensin I in turn being degraded to the hypertensive octapeptide angiotensin II in the lungs, the kidneys or other tissues. The various effects of angiotensin II, such as, for example, vasoconstriction, Na+ retention in the kidney, release of aldosterone in the adrenals and an increase in the tonicity of the sympathic nervous system have a synergistic action in the sense of increasing blood pressure.

Angiontensin II moreover has the property of promoting growth and multiplication of cells, such as, for example, of cardiac muscle cells and smooth muscle cells, these growing and proliferating to an increased extent in various disease states (for example hypertension, atherosclerosis and cardiac insufficiency).

Possible use for intervention in the renin-angiotensin system (RAS) is, in addition to inhibition of renin activity, inhibition of the activity of angiotensin converting enzyme (ACE) and blockage of angiotensin II receptors.

The invention relates to sulphonylbenzyl-substituted imidazopyridines of the general formula (I)

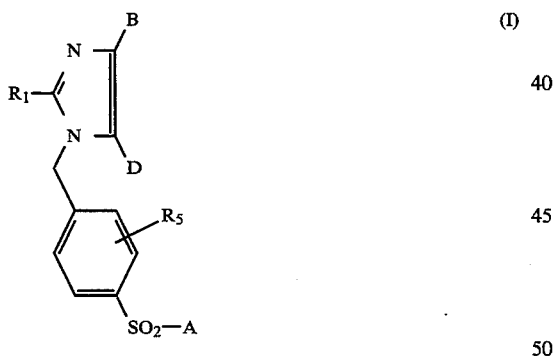

in which
  $R^1$ represents straight-chain or branched alkyl or alkenyl having in each case up to 8 carbon atoms, which are optionally substituted by cycloalkyl having 3 to 6 carbon atoms, or represents cycloalkyl having 3 to 8 carbon atoms,
  B and D together form a heterocyclic radical of the formula

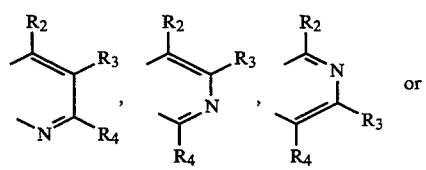

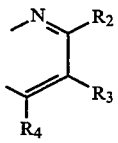

wherein
  $R^2$ and $R^3$ are identical or different and denote hydrogen, halogen or straight-chain or branched alkyl having up to 8 carbon atoms,
  $R^4$ has the abovementioned meaning of $R^2$ and $R^3$ and is identical to or different from these, or denotes a group of the formula —CO—$R^6$,
  wherein
    $R^5$ denotes hydroxyl, straight-chain or branched alkoxy having up to 8 carbon atoms, phenoxy, benzyloxy or a group of the formula —$NR^7R^6$,
    wherein
      $R^7$ and $R^8$ are identical or different and denote hydrogen or straight-chain or branched alkyl having up to 6 carbon atoms or phenyl,
  $R^5$ represents hydrogen, halogen or straight-chain or branched alkyl having up to 8 carbon atoms, or represents straight-chain or branched perfluoroalkyl having up to 6 carbon atoms, or represents a group of the formula —OX,
    wherein
      X denotes hydrogen, benzyl, a hydroxyl protective group or denotes straight-chain or branched alkyl having up to 8 carbon atoms,
  A represents a 3- to 8-membered saturated heterocyclic radical which is bonded via the nitrogen atom, contains up to 2 further heteroatoms from the series comprising S, N and O and is optionally substituted up to twice, in an identical or different manner, by perfluoroalkyl having up to 5 carbon atoms or by a radical of the formula

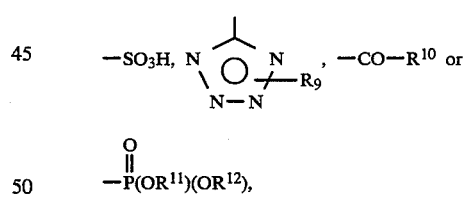

$$-\overset{O}{\underset{\|}{P}}(OR^{11})(OR^{12}),$$

wherein
  $R^9$ denotes hydrogen, straight-chain or branched alkyl having up to 6 carbon atoms or triphenylmethyl,
  $R^{10}$ has the abovementioned meaning of $R^6$ and is identical to or different from this radical and
  $R^{11}$ and $R^{12}$ are identical or different and denote hydrogen, straight-chain or branched alkyl having up to 8 carbon atoms or phenyl,
and salts thereof.

The sulphonylbenzyl-substituted imidazopyridines according to the invention can also be present in the form of their salts. In general, salts with organic or inorganic bases or acids may be mentioned here.

Physiologically acceptable salts are preferred in the context of the present invention. Physiologically acceptable salts of the sulphonylbenzyl-substituted imidazopyridines can be salts of the substances according to the invention with mineral acids, carboxylic acids or sulphonic acids. Particularly preferred salts are, for example, salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, citric acid, fumaric acid, maleic acid or benzoic acid.

Physiologically acceptable salts can likewise be metal salts or ammonium salts of the compounds according to the invention which have a free carboxyl group. Particularly preferred salts are, for example, the sodium, potassium, magnesium or calcium salts, and ammonium salts which are derived from ammonia or organic amines, such as, for example, ethylamine, di- or triethylamine, di- or triethanolamine, dicyclohexylamine, dimethylaminoethanol, arginine, lysine or ethylenediamine.

The compounds according to the invention can exist in stereoisomeric forms, either as the enantiomer or as the diastereomer. The invention relates both to the enantiomers or diastereomers and to their particular mixtures. The racemic forms, like the diastereomers, can be separated into the stereoisomerically uniform constituents in a known manner [compare E. L. Eliel, Stereochemistry of Carbon Compounds, McGraw Hill, 1962].

A 3- to 8-membered saturated heterocyclic radical which is bonded via N and moreover can contain up to 2 oxygen, sulphur and/or nitrogen atoms as hetereoatoms in general represents azetidinyl, piperidyl, morphonyl, piperazinyl or pyrrolidyl. 5- or 6-membered rings having one oxygen and/or up to 2 nitrogen atoms are preferred, such as, for example, azetidinyl, piperidyl, morpholinyl or piperazinyl or pyrrolidinyl. Piperidyl and pyrrolidinyl are particularly preferred.

Hydroxyl protective group in the context of the abovementioned definition in general represents a protective group of the series: trimethylsilyl, triethylsilyl, triisopropylsilyl, tert-butyldimethylsilyl, tert-butyldiphenylsilyl, triphenylsilyl, trimethylsilylethoxycarbonyl, benzyl, triphenylmethyl (trityl), monomethoxytrityl (MMTr), dimethoxytrityl (DMTr), benzyloxycarbonyl, 2-nitrobenzyl, 4-nitrobenzyl, 2-nitrobenzyloxycarbonyl, 4-nitrobenzyloxycarbonyl, tert-butoxycarbonyl, allyloxycarbonyl, 4-methoxybenzyl, 4-methoxybenzyloxycarbonyl, formyl, acetyl, trichloroacetyl, 2,2,2-trichloroethoxycarbonyl, 2,4-dimethoxybenzyl, 2,4-dimethoxybenzyloxycarbonyl, methoxymethyl, methylthiomethyl, methoxyethoxymethyl, [2-(trimethylsilyl)-ethoxy]methyl, 2-(methylthiomethoxy)ethoxycarbonyl, tetrahydropyranyl, benzoyl, 4-methylbenzoyl, 4-nitrobenzoyl, 4-fluorobenzoyl, 4-chlorobenzoyl and 4-methoxybenzoyl. Acetyl, benzyl and tert-butyldimethylsilyl are preferred.

Preferred compounds of the general formula (I) are those
in which
$R^1$ represents straight-chain or branched alkyl or alkenyl having up in each case up to 6 carbon atoms, which are optionally substituted by cyclopropyl, cyclobutyl, cyclopentyl or cyclohexyl, or represents cyclopropyl, cyclopentyl or cyclohexyl, B and D together form a heterocyclic radical of the formula

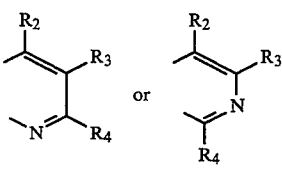

wherein
$R^2$ and $R^3$ are identical or different and denote hydrogen, fluorine, chlorine, bromine or straight-chain or branched alkyl having up to 6 carbon atoms, $R^4$ has the abovementioned meaning of $R^2$ and $R^3$ and is identical to or different from these radicals, or denotes a group of the formula —CO—$R^6$,
wherein
$R^6$ denotes hydroxyl, straight-chain or branched alkoxy having up to 6 carbon atoms, phenoxy, benzyloxy or a group of the formula —N$R^7R^8$,
wherein
$R^7$ and $R^8$ are identical or different and denote hydrogen or straight-chain or branched alkyl having up to 4 carbon atoms, $R^5$ represents hydrogen, fluorine, chlorine, bromine or straight-chain or branched alkyl having up to 6 carbon atoms, or represents straight-chain or branched perfluoroalkyl having up to 4 carbon atoms, or represents a group of the formula —OX,
wherein
X denotes hydrogen, benzyl, acetyl, or denotes straight-chain or branched alkyl having up to 6 carbon atoms, A represents azetidinyl, piperidyl, pyrrolidinyl or morpholinyl, which are bonded via the nitrogen atom and are optionally substituted by trifluoromethyl or by a radical of the formula —SO$_3$H,

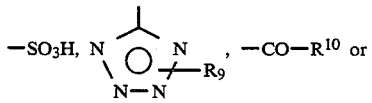

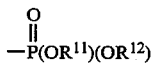

wherein
$R^9$ denotes hydrogen, straight-chain or branched alkyl having up to 4 carbon atoms or triphenylmethyl, $R^{10}$ has the abovementioned meaning of $R^6$ and is identical to or different from this radical and $R^{11}$ and $R^{12}$ are identical or different and denote hydrogen, straight-chain or branched alkyl having up to 6 carbon atoms or phenyl,
and salts thereof.

Particularly preferred compounds of the general formula (I) are those
in which
$R^1$ represents straight-chain or branched alkyl or alkenyl having in each case up to 4 carbon atoms, or cyclopropyl, B and D together form a heterocyclic radical of the formula

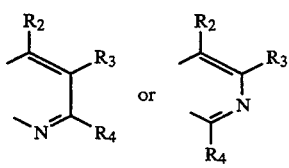

wherein

R² and R³ are identical or different and denote hydrogen, fluorine, chlorine, bromine or straight-chain or branched alkyl having up to 4 carbon atoms, R⁴ has the abovementioned meaning of R² and R³ and is identical to or different from these radicals, or denotes a group of the formula —CO—R⁶, wherein R⁶ denotes hydroxyl, straight-chain or branched alkoxy having up to 4 carbon atoms, phenoxy, benzyloxy or a group of the formula —NR⁷R⁸, wherein R⁷ and R⁸ are identical or different and denote hydrogen or straight-chain or branched alkyl having up to 3 carbon atoms, R⁵ represents hydrogen, fluorine, chlorine or straight-chain or branched alkyl having up to 4 carbon atoms, or represent straight-chain or branched perfluoroalkyl having up to 3 carbon atoms, or represents a group of the formula —OX, wherein X denotes hydrogen, benzyl, acetyl or denotes straight-chain or branched alkyl having up to 6 carbon atoms, A represents azetidinyl, piperidyl or pyrrolidinyl, which are bonded via the nitrogen atom and are optionally substituted by trifluoromethyl or by a radical of the formula —SO₃H,

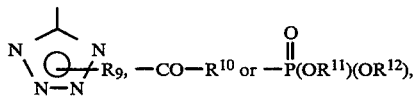

wherein

R⁹ denotes hydrogen, methyl, ethyl or triphenylmethyl,

R¹⁰ has the abovementioned meaning of R⁶ and is identical to or different from this radical and R¹¹ and R¹² are identical or different and denote hydrogen, straight-chain or branched alkyl having up to 4 carbon atoms or phenyl, and salts thereof.

A process has furthermore been found for the preparation of the compounds of the general formula (I) according to the invention, characterised in that sulphonylbenzyl compounds of the general formula (II)

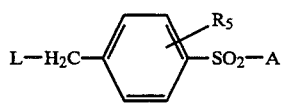

in which

A and R⁵ have the abovementioned meaning and

L represents halogen, preferably bromine, are reacted with imidazopyridines of the general formula (III)

in which

R¹, B and D have the abovementioned meaning, in inert solvents in the presence of a base, and both the substituents R¹ and R⁵ and those of the heterocyclic rings (A, B and D) are varied, if appropriate, by customary methods, for example by alkylation or hydrolysis.

The process according to the invention can be illustrated by way of example by the following equation:

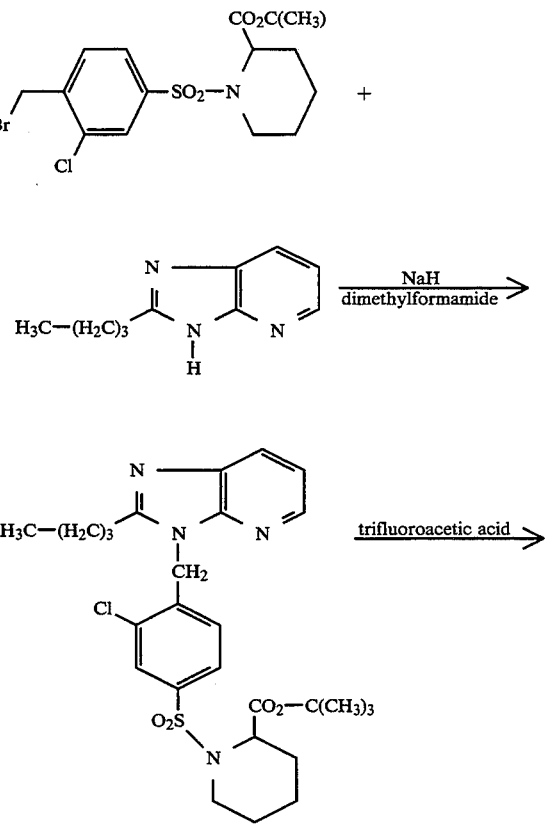

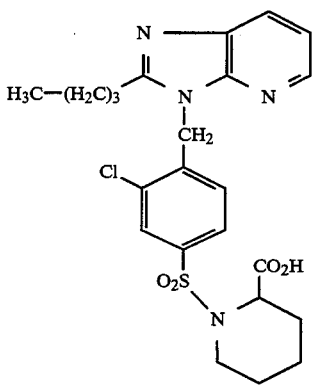

Suitable solvents for the process are customary organic solvents which do not change under the reaction conditions. These include, preferably, ethers such as diethyl ether, dioxane, tetrahydrofuran or glycol dimethyl ether, or hydrocarbons, such as benzene, toluene, xylene, hexane, cyclohexane or petroleum fractions, or halogenohydrocarbons, such as methylene chloride, chloroform, carbon tetrachloride, dichloroethylene, trichloroethylene or chlorobenzene, or ethyl acetate, triethylamine, pyridine, dimethyl sulphoxide, dimethylformamide, hexamethylphosphoric acid triamide, acetonitrile, acetone or nitromethane. It is likewise possible to use mixtures of the solvents mentioned. Tetrahydrofuran, methylene chloride, toluene or dimethylformamide are preferred for the various steps.

Inorganic or organic bases can in general be employed as bases for the process according to the invention. These include, preferably, alkali metal hydroxides, such as, for example, sodium hydroxide or potassium hydroxide, alkaline earth metal hydroxides, such as, for example, barium hydroxide, alkali metal carbonates, such as sodium carbonate or potassium carbonate, alkaline earth metal carbonates, such as calcium carbonate, or alkali metal or alkaline earth metal alcoholates or amides, such as sodium methanolate or potassium methanolate, sodium ethanolate or potassium ethanolate, potassium tert-butylate or lithium diisopropylamide (LDA), or organic amines (trialkyl($C_1$-$C_6$)amines), such as triethylamine, or heterocyclic compounds, such as 1,4-diazabicyclo[2.2.2]octane (DABCO), 1,8-diazabicyclo[5.4.0]undec-7-ene (DBU), pyridine, diaminopyridine, methylpiperidine or morpholine.

It is also possible to employ alkali metals, such as sodium, or hydrides thereof, such as sodium hydride, as the bases. Sodium hydride, lithium diisopropylamide (LDA) and DBU are preferred.

The base is in general employed in an amount of 0.05 mol to 10 mol, preferably 1 mol to 2 mol, per mol of the compound of the formula (III).

The process according to the invention is in general carried out in a temperature range from −100° C. to +100° C., preferably from 0° C. to +30° C.

The process according to the invention is in general carried out under normal pressure. However, it is also possible to carry out the process under increased pressure or under reduced pressure (for example in a range from 0.5 to 5 bar).

Suitable bases for the hydrolysis are the customary inorganic bases. These include, preferably, alkali metal hydroxides or alkaline earth metal hydroxides, such as, for example, sodium hydroxide, potassium hydroxide or barium hydroxide, or alkali metal carbonates, such as sodium carbonate or potassium carbonate or sodium hydrogen carbonate, or alkali metal alcoholates, such as sodium methanolate, sodium ethanolate, potassium methanolate, potassium ethanolate or potassium tert-butanolate. Sodium hydroxide or potassium hydroxide are particularly preferably employed.

Suitable solvents for the hydrolysis are water or the organic solvents customary for hydrolysis. These include, preferably, alcohols, such as methanol, ethanol, propanol, isopropanol or butanol, or ethers, such as tetrahydrofuran or dioxane, or dimethylformamide or dimethyl sulphoxide. Alcohols, such as methanol, ethanol, propanol or isopropanol, are particularly preferably used. It is also possible to employ mixtures of the solvents mentioned.

The hydrolysis can also be carried out with acids, such as, for example, trifluoroacetic acid, acetic acid, hydrochloric acid, hydrobromic acid, methanesulphonic acid, sulphuric acid or perchloric acid, preferably with trifluoroacetic acid.

The hydrolysis is in general carried out in a temperature range from 0° C. to +100° C., preferably from +20° C. to +80° C.

The hydrolysis is in general carried out under normal pressure. However, it is also possible to carry out the hydrolysis under reduced pressure or under increased pressure (for example from 0.5 to 5 bar).

In carrying out the hydrolysis, the base is in general employed in an amount of 1 to 3 mol, preferably 1 to 1.5 mol, per mol of the ester. Molar amounts of the reactants are particularly preferably used.

In carrying out the reaction, the carboxylates of the compounds according to the invention are formed as intermediate products, which can be isolated, in the first step. The acids according to the invention are obtained by treatment of the carboxylates with customary inorganic acids. These include, preferably, mineral acids, such as, for example, hydrochloric acid, hydrobromic acid, sulphuric acid or phosphoric acid. In the preparation of the carboxylic acids, it has proved advantageous here to acidify the basic reaction mixture of the hydrolysis in a second step without isolation of the carboxylates. The acids can then be isolated in a customary manner. In the case of the basic heterocyclic compounds, the salts of the heterocyclic compounds with the inorganic acids can also be obtained by treatment of the solutions of the carboxylates with the abovementioned acids.

The alkylation is in general carried out with alkylating agents, such as, for example, ($C_1$-$C_6$)-alkyl halides, sulphonic acid esters or substituted or unsubstituted ($C_1$-$C_6$)-dialkyl- or ($C_1$-$C_6$)-diarylsulphonates, preferably methyl iodide or dimethyl sulphate.

The alkylation is in general carried out in one of the abovementioned solvents, preferably in dimethylformamide, in a temperature range from 0° C. to +70° C., preferably from 0° C. to +30° C., under normal pressure.

The compounds of the general formula (II) are new and can be prepared, for example, by a process in which, in cases where $R^5 \neq$ —OX, compounds of the general formula (IV)

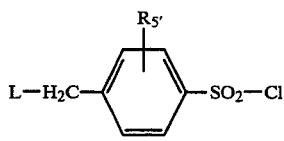

in which
L has the abovementioned meaning and
R5' has the abovementioned meaning,
are reacted with compounds of the general formula (V)

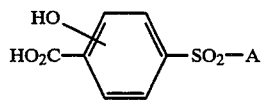

in which A has the abovementioned meaning, in one of the abovementioned solvents in bases, preferably in methylene chloride with triethylamine, under normal pressure and in a temperature range from 40° C. to +120° C., preferably at 0° C., and in cases where $R^5$ represents the group of the formula —OX, carboxy- and hydroxy-disubstituted benzenesulphonic acid chlorides, such as for example 4-carboxy-3-hydroxybenzenesulphochloride, are first reacted with compounds of the general formula (V) to produce compounds of the general formula (VI) (x=H),

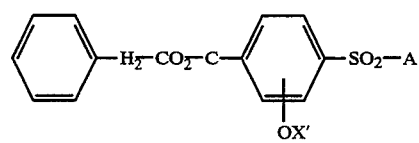

in which
A has the abovementioned meaning, and, by convening the carboxyl group into the corresponding benzyl ester and masking the hydroxyl group by customary methods, these compounds (VI) are then convened into compounds of the general formula (VII)

(VII)

in which
A has the abovementioned meaning and
X' has the abovementioned meaning of X, but does not represent hydrogen, then, in a further step, the benzyl ester of these compounds of the general formula (VII) is reduced to form the hydroxymethyl group, also using known methods and preferably with the aid of sodium borohydride/LiCl in diglyme,
and the product is finally brominated with triphenylphosphine dibromide in one of the abovementioned solvents, preferably dimethylformamide, under an inert gas atmosphere, in a temperature range from 0° C. to room temperature.

The compounds of the general formulae (VI) and (VII) are both new and can be prepared as described above.

The compounds of the general formulae (IV) and (V) are known or can be prepared by a customary method.

The compounds of the general formula (III) are likewise known per se.

The above preparation processes are given merely for illustration. The preparation of the compounds of the general formula (I) according to the invention is not limited to these processes, and any modification of these processes can be used in the same manner for the preparation.

The compounds of the general formula (I) according to the invention exhibit an unforeseeable, useful pharmacological spectrum of action.

The compounds according to the invention have a specific A II antagonistic action, since they inhibit bonding of angiotensin II to A II receptors. They suppress the vasoconstrictive and aldosterone secretion-stimulating effects of angiotensin II. Moreover, they inhibit the proliferation of smooth muscle cells.

They can therefore be employed in medicaments for the treatment of arterial hypertension and atherosclerosis, Moreover, they can be employed for the treatment of coronary heart diseases, cardiac insufficiency, disturbances in cerebral performance, ischaemic cerebral diseases, disturbances in peripheral circulation, functional disturbances of the kidney and adrenals, diseases of the respiratory passages of bronchospastic and vascular origin, sodium retention and oedemas.

The substances moreover have a natriuretic and diuretic action. This action manifests itself in a mobilisation of oedema fluid in cases of pathological increase in fluid of cardiac and non-cardiac origin.

INVESTIGATION OF THE INHIBITION OF CONTRACTION INDUCED BY AGONISTS

Rabbits of both sexes are stunned by a blow to the neck and exsanguinated, or in some cases anaesthetised with Nembutal (about 60–80 mg/kg i.v.) and sacrificed by opening the thorax. The thoracic aorta is removed, freed from attached connective tissue and divided into ring segments 1.5 mm wide, and the segments are introduced individually, under an initial load of about 3.5 g, in 10 ml organ baths containing carbogen-gassed Krebs-Henseleit nutrient solution thermostatically controlled at 37° C. and having the following composition: 119 mmol/l of NaCl; 2.5 mmol/l of $CaCl_2 \times 2H_2O$; 1.2 mmol/l of $KH_2PO_4$; 10 mmol/l of glucose; 4.8 mmol/l of KCl; 1.4 mmol/l of $MgSO_4 \times 7H_2O$ and 25 mmol/l of $NaHCO_3$.

The contractions are recorded isometrically by Statham UC2 cells via bridged amplifiers (ifd Mülheim or DSM Aalen) and are digitised and evaluated by means of an A/D converter (System 570, Keithley Munich). The agonist dose/effect curves (DEC) are plotted hourly. With every DEC, 3 or 4 individual concentrations are applied to the baths at intervals of 4 minutes. The end of the DEC and subsequent wash-out cycles (16 times for in each case about 5 seconds/minute with the above nutrient solution) is followed by a 28-minute rest or incubation phase, during which the contractions as a rule reach the starting value again.

The level of the third DEC in the normal case is used as the reference parameter for evaluation of the test substance which is to be investigated in subsequent passes and is applied to the baths for the following DECs at the start of the incubation time at a dosage which increases each time. Each aortic ring is stimulated over the whole day with always the same agonist.

Agonists and their standard concentrations (Application volume per individual dose = 100 μl):

| | | |
|---|---|---|
| KCl | 22.7;32.7;42.7;52.7 | mmol/l |

-continued

| Agonists and their standard concentrations (Application volume per individual dose = 100 μl): | | |
|---|---|---|
| 1-Noradrenaline | $3 \times 10^{-9}; 3 \times 10^{-8}; 3 \times 10^{-7}; 3 \times 10^{-6}$ | g/ml |
| Serotonin | $10^{-8}; 10^{-7}; 10^{-6}; 10^{-5}$ | g/ml |
| B-HT 920 | $10^{-7}; 10^{-6}; 10^{-5}$ | g/ml |
| Methoxamine | $10^{-7}; 10^{-6}; 10^{-5}$ | g/ml |
| Angiotensin II | $3 \times 10^{-9}; 10^{-8}; 3 \times 10^{-8}; 10^{-7}$ | g/ml |

For calculation of the $IC_{50}$ (concentration at which the substance under investigation causes 50% inhibition), the particular effect at the 3rd=submaximal agonist concentration is taken as the basis.

The compounds according to the invention inhibit angiotensin II-induced contraction of the isolated rabbit aorta as a function of the dose. The contraction induced by potassium depolarisation or other agonists was not inhibited or was inhibited only slightly at high concentrations.

TABLE A

Inhibition of vascular contraction on isolated aortic rings of the rabbit in vitro
$IC_{50}$ [nM] against contractions induced by:

| Ex. No.: | AII |
|---|---|
| 5 | 40 |
| 2 | 326 |
| 19 | 6 |
| 20 | 6 |
| 31 | 4 |
| 39 | 3 |
| 41 | 3 |

BLOOD PRESSURE MEASUREMENTS ON ANGIOTENSIN II-INFUSED RATS

Male Wistar rats (Moellegaard, Copenhagen, Denmark) with a body weight of 300-350 g are anaesthetised with thiopental (100 mg/kg i.p.). After tracheotomy, a catheter for blood pressure measurement is inserted into the femoral artery and a catheter for angiotensin II infusion and a catheter for administration of the substance are inserted into the femoral veins. After administration of the ganglion blocker pentolinium (5 mg/kg i.v.), the angiotensin II infusion (0.3 μg/kg/minute) is started. As soon as the blood pressure values have reached a stable plateau, the test substances are administered either intravenously, or orally as a suspension or solution in 0.5% of tylose. The changes in blood pressure under the influence of the substance are shown as the mean values ±SEM in the table.

| Example No. | Dose [mg/kg] p.o. | ΔP [mm Hg] |
|---|---|---|
| 20 | 0.1 | −48 |
| 31 | 0.1 | −62 |
| 39 | 0.1 | −32 |

DETERMINATION OF THE ANTIHYPERTENSIVE ACTIVITY ON CONSCIOUS HYPERTENSIVE RATS

The oral antihypertensive activity of the compounds according to the invention was tested on conscious rats with surgically induced unilateral renal artery stenosis. For this, the right renal artery was constricted with a silver clip of 0.18 nun internal diameter. With this form of hypertension, the plasma renin activity is increased in the first six weeks after the intervention.

The arterial blood pressure of these animals was measured bloodlessly with the "tail cuff" at defined intervals of time after administration of the substance. The substances to be tested were administered intragastrally ("orally") by a stomach tube in various doses as a suspension in a tylose suspension. The compounds according to the invention reduce the arterial blood pressure of hypertensive rats in a clinically relevant dosage.

The compounds according to the invention moreover inhibit specific bonding of radioactive angiotensin II as a function of the concentration.

INTERACTION OF THE COMPOUNDS ACCORDING TO THE INVENTION WITH THE ANGIOTENSIN II RECEPTOR ON MEMBRANE FRACTIONS OF THE ADRENAL CORTEX (CATTLE)

Adrenal cortices from cattle (AC), which are freshly removed and carefully freed from medulla of the capsule, are comminuted to a coarse membrane homogenate in sucrose solution (0.32M) with the aid of an Ultra-Turrax (Janke & Kunkel, Staufen i.B.), and the homogenate is partly purified to membrane fractions in two centrifugation steps.

The investigations on receptor bonding are carried out on partly purified membrane fractions of bovine AC with radioactive angiotensin II in an assay volume of 0.25 ml, which specifically contains the partly purified membranes (50–80 μg), 3H-angiotensin II (3–5 nM), test buffer solution (50 mM Tris, pH 7.2), 5 mM $MgCl_2$ and the substances to be investigated. After an incubation time of 60 minutes at room temperature, the non-bonded radioactivity of the samples is separated off by means of a moistened glass fibre filter (Whatman GF/C) and, after the protein has been washed with ice-cold buffer solution (50 mM Tris/HCl, pH 7.4, 5% PEG 6000), the bonded radioactivity is measured by spectrophotometry in a scintillation cocktail. The raw data were analysed for $K_i$ and $IC_{50}$ values by computer programs ($K_i$: $IC_{50}$ values corrected for the radioactivity used; $IC_{50}$ values: concentration at which the substance under investigation causes 50% inhibition of the specific bonding of the radio ligand).

Example 5 Ki=550 nM
Example 2 Ki=1000 nM

INVESTIGATION OF THE INHIBITION OF PROLIFERATIONS OF SMOOTH MUSCLE CELLS BY THE COMPOUNDS ACCORDING TO THE INVENTION

Smooth muscle cells obtained from the aortas of rats or pigs by the media explantate technique [R. Ross, J. Cell. Biol. 50, 172, 1971] are used to determine the antiproliferative action of the compounds.

The cells are sown in suitable culture dishes, as a rule 24-hole plates, and cultured for 2–3 days in medium 199 with 7.5% of FCS and 7.5% of NCS, 2 mM L-glutamine and 15 mM HEPES, pH 7.4, in 5% $CO_2$ at 37° C. The cells are then synchronised for 2–3 days by withdrawal of the serum, and subsequently stimulated into growth with AII, serum or other factors. Test compounds are added at the same time. After 16–20 hours, 1 μCi 3H-thymidine is added, and after a further 4 hours, the incorporation of this substance into the TCA-precipitatable DNA of the cells is determined.

| Example No. | % Inhibition at $10^{-6}$ M |
| --- | --- |
| 5 | 70 |
| 2 | 40 |

TEST FOR NATRIURETIC ACTION

Fasting Wistar rats are treated orally with the test substance (suspended in tylose solution). The urine excreted is then collected for 6 hours in diuresis cages. The concentration of sodium and potassium in the urine is determined by flame photometry.

The new active compounds can be converted in a known manner into the customary formulations, such as tablets, coated tablets, pills, granules, aerosols, syrups, emulsions, suspensions and solutions, using inert, nontoxic, pharmaceutically suitable excipients or solvents. The therapeutically active compound should in each case be present here in a concentration of about 0.5 to 90% by weight of the total mixture, that is to say in amounts which are sufficient to achieve the stated dosage range.

The formulations are prepared, for example, by extending the active compounds with solvents and/or excipients, if appropriate using emulsifying agents and/or dispersing agents, and, for example, in the case where water is used as the diluent, organic solvents can be used as auxiliary solvents if appropriate.

The active compounds are administered in the customary manner, preferably orally or parenterally, in particular perlingually or intravenously.

In the case of parenteral administration, solutions of the active compound using suitable liquid excipient materials can be employed.

In general, it has proved advantageous, in the case of intravenous administration, to administer amounts of about 0.001 to 1 mg/kg, preferably about 0.01 to 0.5 mg/kg of body weight to achieve effective results, and in the case of oral administration, the dosage is about 0.01 to 20 mg/kg, preferably 0.1 to 10 mg/kg of body weight.

Nevertheless, it may at times be necessary to deviate from the amounts mentioned, and in particular to do so as a function of the body weight or the nature of the administration route, the behaviour of the individual towards the medicament, the nature of its formulation and the time or interval at which administration takes place. Thus in some cases it may be sufficient to manage with less than the abovementioned minimum amount, while in other cases the upper limit mentioned must be exceeded. Where relatively large amounts are administered, it may be advisable to divide these into several individual doses over the day.

| Mobile phase mixtures: | | |
| --- | --- | --- |
| a | = methylene chloride/methanol | 10:1 |
| b | = petroleum ether/ethyl acetate | 1:1 |
| c | = ethyl acetate/petroleum ether | 2:1 |
| d | = methylene chloride/methanol | 4:1 |
| e | = toluene/methanol | 10:1 |

STARTING COMPOUNDS

Example I 4-(Bromomethyl)benzenesulphonyl chloride

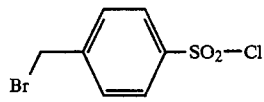

38.1 g (0.2 mol) of 4-methylbenzenesulphonyl chloride are dissolved in 300 ml of carbon tetrachloride, 35.6 g (0.2 mol) of N-bromosuccinimide are added and, after addition of 0.2 g (1.2 mmol) of azobisisobutyronitrile (ABU), the mixture is heated under reflux for 4 hours. After cooling, the solids are filtered off and the filtrate is freed from the solvent. Flash chromatography (petroleum ether/toluene 4:1, 50 μm particle size) and subsequent recrystallisation from 100 ml of cyclohexane give 24.0 g (45% of theory) of the title compound.

$R_f$=0.75 (toluene)

Example II 4-(Bromomethyl)-3-chlorobenzenesulphonyl chloride

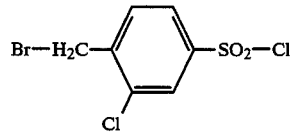

45.9 g (0.2 mol) of sodium 3-chloro-4-methylbenzenesulphonate are mixed with 83.3 g (0.4 mol) of phosphorus pentachloride and the mixture is heated at an oil bath temperature of 140° C. for 30 minutes. 500 ml of toluene are added, while the mixture is hot, and the resulting solution is heated to the boiling point and, after cooling, poured onto ice. The organic phase is separated off and washed with water (2×200 ml). After drying over MgSO$_4$, the organic phase is filtered and all the volatile substances are stripped off in vacuo. The residue obtained is purified by flash chromatography (petroluem ether/toluene 4:1, 50μ particle size). 24.9 g of a product, which is further reacted immediately, are obtained:

The product is taken up in 200 ml of carbon tetrachloride and, after addition of 19.6 g (0.11 mol) of N-bromosuccinimide and 0.1 g (0.6 mmol) of ABN, the mixture is heated under reflux for 6 hours. After cooling, the solids are filtered off and the filtrate is freed from the solvent. Flash chromatography (petroluem ether/toluene ene 4:1, 50μ particle size) gives 21.2 g (35%) of the title compound.

$R_f$=0.32 (petroluem ether/methylene chloride 4:1)

Example III 4-(Bromomethyl)-benzenesulphonyl-N-pyrrolidinide

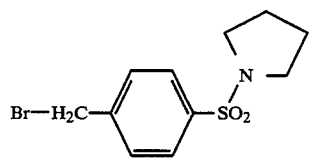

5.3 g (0.02 mol) of the compound from Example I are dissolved in 200 ml of methylene chloride and 4.0 g (0.04 mol) of triethylamine, and, after addition of 1.4 g (0.02 mol) of pyrrolidine in 50 ml of methylene chloride at 0° C., the mixture is subsequently stirred at 0° C. for 1 hour. It is extracted with 2N HCl (2×100 ml) and H₂O (2×100 ml), the extract is dried over MgSO₄ and filtered, and all the volatile contents are evaporated off in vacuo.

Yield: 5.4 g (89% of theory)
$R_f$=0.09 (toluene)

Example IV 4-(Bromomethyl)benzenesulphonyl-N-piperidinide

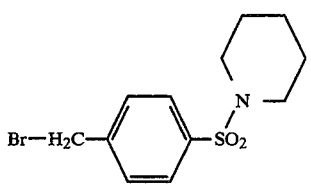

Analogously to the instructions of Example III, 1.0 g (81% of theory) of the title compound is obtained from 1.1 g (4 mmol) of the compound from Example I and 0.34 g (4 mmol) of piperidine.

$R_f$=0.14 (toluene)

Example V (S)-4-(Bromomethyl)-benzenesulphonyl-N-2-(tert-butoxycarbonyl)pyrrolidinide

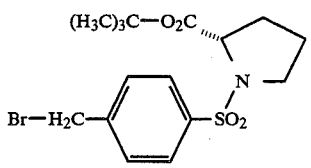

Analogously to the instructions of Example III, 9.1 g (84% of theory) of the title compound are obtained from 7.25 g (27 mmol) of the compound from Example I and 4.6 g (27 mmol) of S-proline tert-butyl ester.
$R_f$=0.66 (petroleum ether/ethyl acetate 7:3)

Example VI rac-4-(Bromomethyl)-benzenesulphonyl-N-2-(tert-butoxycarbonyl)piperidinide

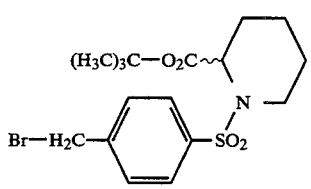

Analogously to the instructions of Example III, 7.4 g (59% of theory) of the title compound are obtained from 8.0 g (30 mmol) of the compound from Example I and 5.5 g (30 mmol) of rac-pipecolinic acid tert-butyl ester.

$R_f$=0.53 (petroleum ether/ethyl acetate 5:1)

Example VII (S)-4-(Bromomethyl)-3-chlorobenzenesulphonyl-N-2-(tert-butoxycarbonyl)pyrrolidinide

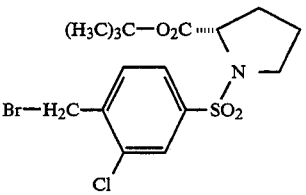

Analogously to the instructions of Example III, 13.9 g (96% of theory) of the title compound are obtained from 10.0 g (33 mmol) of the compound from Example II and 5.7 g (33 mmol) of S-proline tert-butyl ester.

$R_f$=0.55 (petroleum ether/ethyl acetate 7:3)

Example VIII rac-4-(Bromomethyl)-3-chlorobenzenesulphonyl-N-2-(tert-butoxycarbonyl)piperidinide

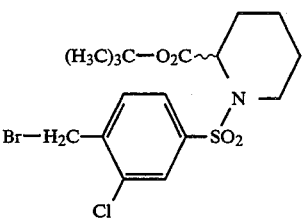

Analogously to the instructions of Example III, 14.6 g (98% of theory) of the title compound are obtained from 10.0 g (33 mmol) of the compound from Example II and 6.1 g (33 mmol) of rac-pipecolinic acid tert-butyl ester.

$R_f$=0.6 (petroleum ether/ethyl acetate 7:3)

Example IX N-Trifluoroacetyl-L-prolinamide

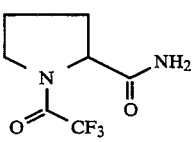

30 g (0.142 mol) of trifluoroacetylproline are initially introduced into 150 ml of dimethylformamide under an inert gas. 142.6 ml (0.1704 mol) of 38% propane phosphonic acid anhydride in ethyl acetate are added at −20° C. Ammonia is passed in until the mixture is saturated, a white precipitate separating out after 30 minutes. The mixture is thawed under a weak stream of ammonia. The entire reaction mixture is then poured into 600 ml of H₂O and acidified to pH 4 with concentrated acetic acid. It is extracted by shaking 4× with 200 ml of methylene chloride and 3× with 200 ml of ether. The combined organic phases are dried with magnesium sulphate and the solvent is stripped off. The residues are chromatographed together over silica gel 60 F254, methylene chloride/methanol (10:1). The fractions containing the product are freed from the solvent on a rotary evaporator.

17.12 g of the title compound (57% of theory) are obtained;

$R_f$: 0.345 (toluene/ethyl acetate/CH$_3$COOH) 20:20:1

Example X

2-Cyano-N-trifluoroacetyl-pyrrolidine

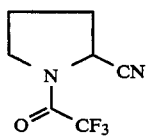

40 g (0.19 mol) of the product from Example IX and 45 g= 46 ml (0.57 mol) of pyridine are initially introduced into 300 ml of tetrahydrofuran under an inert gas. 48 g=32.25 ml (0.228 mol) of trifluoroacetic anhydride are added dropwise at 0° C. The reaction mixture is subsequently stirred at 0° C. for 30 minutes and at room temperature for 90 minutes. It is then introduced into 1 l of 1N hydrochloric acid and extracted by shaking 3× with 200 ml of methylene chloride. The combined organic phases are extracted by shaking with 200 ml of saturated NaCl solution and dried over magnesium sulphate. The solvent is stripped off and the residue is chromatographed on silica gel 60 F254. Petroleum ether/ethyl acetate/acetic acid (1600:200:5). The fractions containing the product are concentrated. 32.4 g of the title compound (88.8% of theory) are obtained.

$R_f$: 0.57 (petroleum ether/ethyl acetate 7:3)

Example XI

2-Tetrazolyl-N-trifluoroacetyl-pyrrolidine

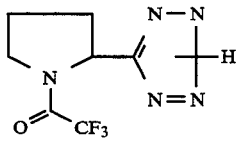

31.35 g=32.6 ml (0.26 mol) of diethylaluminium chloride are initially introduced into 65 ml of toluene under an inert gas. 29.95 g=34.04 ml (0.26 mol) of trimethylsilyl azide are added at room temperature, and the mixture is subsequently stirred at room temperature for 10 minutes. 25 g (0.13 mol) of the product from Example X, dissolved in 65 ml of toluene, are added at 0° C. The reaction mixture is stirred at 0° C. for 30 minutes, at room temperature for 120 minutes and at 40° C. for 60 minutes. Saturated potassium fluoride solution is added to the cooled mixture until no further evolution of gas is detectable.

The reaction mixture is introduced into 600 ml of H$_2$O, acidified to pH 4 and extracted 3× with 100 ml of ethyl acetate. 50 ml of n-hexane are added to the combined organic phases. In order to remove the azides, about ⅓ of the solvent is distilled off over a distillation bridge, without cooling. The residue is dried over magnesium sulphate and freed from the solvent in a rotary evaporator.

18.54 g of the title compound (60.6% of theory) are obtained.

$R_f$: 0.4 (toluene/ethyl acetate 1:1).

Example XII

N-Trifluoroacetyl-2-[N-trityl-tetrazolyl]pyrrolidine

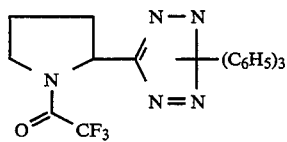

16.43 g (0.069 mol) of the product from Example XI and 10.47 g=14.35 ml (0.1035 mol) of triethylamine are initially introduced into 70 ml of methylene chloride. 19.83 g (0.069 mol) of triphenylmethyl chloride are then added. The reaction mixture is subsequently stirred at room temperature for 1.5 hours, diluted with methylene chloride and extracted with buffer solution of pH 5 (3×50 ml). The organic phase is dried over magnesium sulphate. The solvent is stripped off on a rotary evaporator. The residue is stirred with ether. The resulting crystals are filtered off with suction and dried.

24.65 g of the title compound (75% of theory) are obtained.

$R_f$: 0.53 (petroleum ether/ethyl acetate 7:3).

Example XIII 2-(N-Trityl-tetrazolyl)pyrrolidine

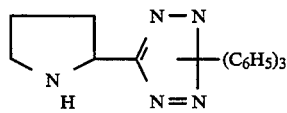

24 g (0.05 mol) of the product from Example XII are initially introduced into 100 ml of ethanol under an inert gas. 2.84 g (0.075 mol) of sodium borohydride are added in portions at 0° C. The mixture is thawed and stirred at room temperature for 1 hour. 6 ml of acetic acid are added and the entire reaction mixture is introduced into 500 ml of buffer solution of pH 9. The mixture is extracted with 3×75 ml of methylene chloride. The combined organic phases are dried over magnesium sulphate and freed from the solvent on a rotary evaporator. The residue is chromatographed on silica gel 60 F 254. Petroleum ether/ethyl acetate (7:3). The corresponding fractions are concentrated and dried.

7.16 g of the title compound (37.5% of theory) are obtained.

$R_f$: 0.22 (ethyl acetate).

Example XIV

4-Bromomethyl-3-chlorobenzenesulphonic acid 2-[trityltetrazolyl]pyrrolidinide

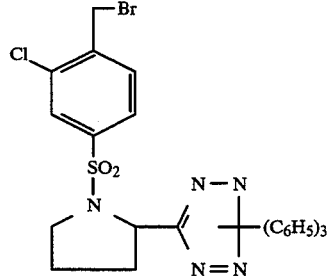

Analogously to the instructions of Example III, 6.49 g of the title compound (95% of theory) are obtained from 3.19 g (10.5 mmol) of the compound from Example II and 4 g (10.5 mmol) of the compound from Example XIII. $R_f$: 0.53 (petroleum ether/ethyl acetate 7:3).

Example XV 4-(Bromomethyl)-3-fluorobenzenesulphonyl chloride 20.9 g (0.1 mol) of 3-fluoro-4-methylbenzenesulphonyl chloride are taken up in 200 ml of carbon tetrachloride and, after addition of 19.6 g (0.11 mol) of N-bromosuccinimide and 0.3 g of dibenzoyl peroxide, the mixture is heated under reflux for 5 hours. After cooling, the solids are filtered off and the filtrate is freed from the solvent. Flash chromatography using petroleum ether/toluene (4:1), 50 μm particle size, gives 12.4 g (44% of theory) of the title compound.

$R_f$: 0.42 (petroleum ether/toluene 3:1).

Example XVI 4-(Bromomethyl)-3-trifluoromethylbenzenesulphonyl chloride 64.6 g (0.25 mol) of 3-trifluoromethyl-4-methylbenzenesulphonyl chloride are taken up in 500 ml of carbon tetrachloride and, after addition of 44.5 g (0.25 mol) of N-bromosuccinimide and 0.4 g of ABN, the mixture is heated under reflux for 24 hours. After cooling, the solids are filtered off and the filtrate is freed from the solvent. Flash chromatography using petroleum ether/toluene (4:1), 50 μm particle size, gives 33.9 g (40% of theory) of the title compound.

$R_f$: 0.41 (petroleum ether/toluene 3:1).

Example XVII (S)-4-(Bromomethyl)-3-fluorobenzenesulphonyl-N-2-(tert-butoxy-carbonyl)pyrrolidinide Analogously to the instructions from Example III, 12.7 g (100% of theory) of the title compound are obtained from 8.6 g (30 mmol) of the compound from Example XV and 5.1 g (30 mmol) of S-proline tert-butyl ester.

$R_f$: 0.57 (petroleum ether/ethyl acetate 7:3).

Example XVIII (S)-4-(Bromomethyl)-3-trifluoromethylbenzenesulphonyl-N-2-(tert-butoxycarbonyl)pyrrolidinide Analogously to the instructions of Example III, 23.6 g (100% of theory) of the title compound are obtained from 16.9 g (50 mmol) of the compound from Example XVI and 8.6 g (50 mmol) of S-proline tert-butyl ester.

$R_f$: 0.63 (petroleum ether/ethyl acetate 7:3).

Example XIX (S)-4-carboxy-3-hydroxybenzenesulphonyl-N-2-(tert.-butoxycarbonyl)-pyrrolidinide Analogously to the method of Example III, 30.0 g (81% of theory) of the title compound are obtained from 23.7 g of 4-carboxy-3-hydroxybenzenesulphochloride (100 mmol) and 17.1 g (1 00 mmol) of S-proline tert.-butyl ester.

$R_f$: 0.18 (acetone)

Example XX (S)-4-Benzyloxycarbonyl-3-benzyloxybenzenesulphonic acid N-2-(tert.-butoxycarbonyl)-pyrrolidinide 28.3 g of $K_2CO_3$ (204 mmol) and 25.7 g (150 mmol) of benzyl bromide are added to 25.3 g (68 mmol) of the compound of Example XIX dissolved in 200 ml of DMF. The reaction mixture is stirred for a further 2 hours at 75° C. and cooled. 1 l of water is then added and the mixture is extracted with ethyl acetate (3×400 ml) and the extract washed with water (5×400 ml), dried over $MgSO_4$, filtered and all the volatile components are stripped off in vacuo. The product is purified by flash chromatography (petroleum ether/CH2Cl2 5:1 and petroleum ether/ethyl acetate 6:1, particle size: 50µ) and then purified further by recrystallisation from 600 ml of a solvent mixture (petroleum ether/ethyl acetate 6:1). 35.5 g (95% of theory) of the title compound are obtained.

R$_f$=0.53 (petroleum ether/ethyl acetate 7:3)

Example XXI (S)-4-(Hydroxymethyl)-3-benzyloxybenzenesulphonic acid N-2-(tert.-butoxycarbonyl)-pyrrolidinide

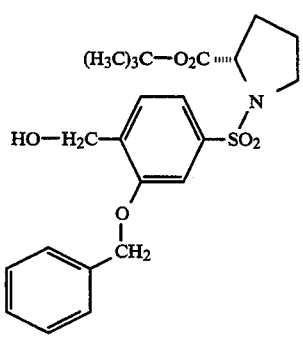

11.03 g (20 mmol) of the compound of Example XX are dissolved in 100 ml of diglyme and, after adding 1.51 g (40 mmol) of sodium borohydride and 1.68 g (40 mmol) of LiCl, the mixture is stirred for 4 hours at 70° C. After cooling, 500 ml of water are added to the reaction mixture, which is then acidified with 1N HCl to a pH of 3. The mixture is extracted with ether (3×300 ml) and the extract is washed with water (6×300 ml), dried over MgSO4 and the filtrate freed from the solvent. The residue is chromatographed on silica gel 60 F 254 (petroleum ether/ethyl acetate (7:3)). The corresponding fractions are concentrated by evaporation and dried. 5.0 g (56% of theory) of the title compound are obtained.

R$_f$=0.36 (petroleum ether/ethyl acetate 7:3)

Example XXII (S)-4-(Bromomethyl)-3-benzyloxybenzenesulphonic acid N-2-(tert.-butoxycarbonyl)-pyrrolidinide

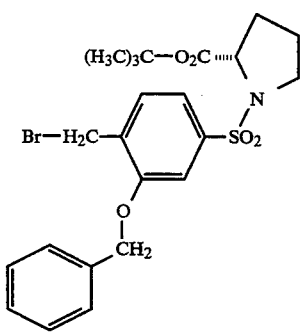

2.24 g (5 mmol) of the compound from Example XXI are initially introduced into 20 ml of absolute DMF under an inch gas. 2.53 g (6 mmol) of triphenylphosphine dibromide are added at 0° C. The reaction mixture is stirred for 1 hour at room temperature. 200 ml of water are added, the mixture is extracted with ethyl acetate (3×80 ml) and the extract is washed with water (5×60 ml), dried over MgSO4, filtered and all the volatile components are stripped off in vacuo. The product is purified by flash chromatography (CH2Cl2, particle size: 50µ) and 2.55 g (100% of theory) of the title compound are obtained.

R$_f$=0.56 (petroleum ether/ethyl acetate 7:3)

PREPARATION EXAMPLES

Example 1 rac-4-[[2-Butyl-imidazo[4,5-b]pyridin]-3-yl]methyl-3-chlorobenzenesulphonyl-N-(2-tert-butoxycarbonyl)piperidinide

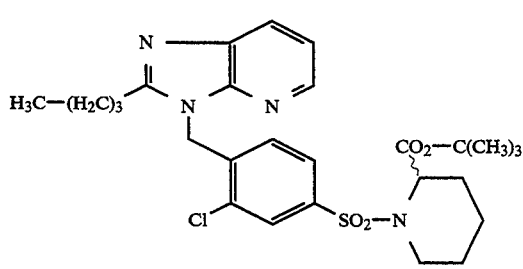

2.3 g (5 mmol) of the compound from Example VIII, dissolved in 8 ml of dimethylformamide, are added to a solution of 613 mg (3.5 mmol) of 2-butylimidazo[4,5-b]pyridine and 105 mg (3.5 mmol) of sodium hydride, and the mixture is subsequently stirred at 20° C. for 3 hours. The reaction mixture is poured onto ice, extracted with ethyl acetate (3×50 ml), washed with saturated NaCl solution (5×50 ml), dried over MgSO4 and filtered, and all the volatile substances are stripped off in vacuo. The residue is purified by flash chromatography (CH2Cl2/ethyl acetate 20:1, 50µ particle size), and the resulting product is then chromatographed over silica gel (ethyl acetate/petroleum ether 1:1, 50µ particle size) to give 563 mg (30% of theory) of the title compound.

R$_f$=0.72 (ethyl acetate/petroleum ether 2:1)

Example 2 rac-4-[{2-Butyl-imidazo[4,5-b]pyridin}-3-yl]methyl-3-chlorobenzenesulphonyl-N-(2-carboxy)piperidinide

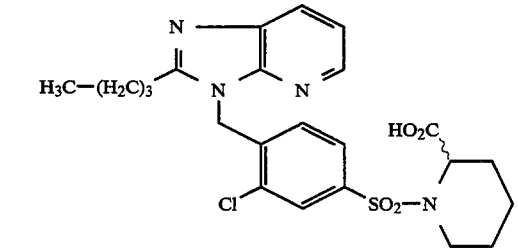

273 mg (0.5 mmol) of the compound from Example 1 are dissolved in 10 ml of methylene chloride, and 2 ml of trifluoroacetic acid are added. The mixture is subsequently stirred at 20° C. for 3 hours, and all the volatile substances are stripped off in vacuo. The residue is taken up in 20 ml of methylene chloride/ether 1:1 and the mixture is then concentrated to dryness. This process is repeated three times to give 300 mg (99% of theory) the title compound as the trifluoroacetate salt.

R$_f$=0.30 (CH2Cl2/MeOH 10:1)

The compounds listed in Tables 1, 2 and 3 are prepared by processes analogous to those described above:

TABLE 1

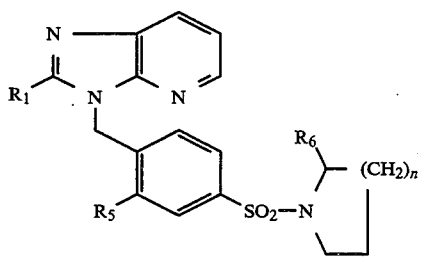

| Ex. No. | R¹ | R⁵ | R⁶ | n | Configuration | $R_f$* | Yield [%] |
|---|---|---|---|---|---|---|---|
| 3 | —(CH₂)₃CH₃ | H | H | 2 | — | 0.13[b] | 29.3 |
| 4 | —(CH₂)₃CH₃ | Cl | —CO₂C(CH₃)₃ | 1 | S | 0.72[c] | 24.3 |
| 5 | —(CH₂)₃CH₃ | Cl | —CO₂H | 1 | S | 0.18[a] | 24.0 |
| 6 | —(CH₂)₃CH₃ | H | —CO₂C(CH₃)₃ | 1 | S | 0.20[d] | 30.0 |
| 7 | —(CH₂)₃CH₃ | H | —CO₂C(CH₃)₃ | 2 | rac | 0.23[d] | 24.0 |
| 8 | —(CH₂)₃CH₃ | H | —CO₂H | 1 | S | 0.16[a] | 96.2 |
| 9 | —(CH₂)₃CH₃ | H | —CO₂H | 2 | rac | 0.22[a] | 99.2 |

TABLE 2

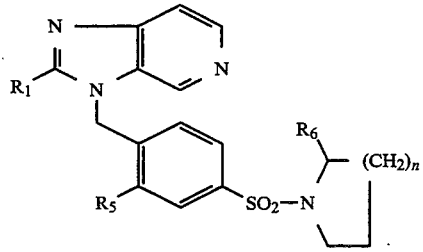

| Ex. No. | R¹ | R⁵ | R⁶ | n | Configuration | $R_f$* | Yield [%] |
|---|---|---|---|---|---|---|---|
| 10 | —(CH₂)₃CH₃ | H | H | 1 | — | 0.14[a] | 6,6 |

TABLE 3

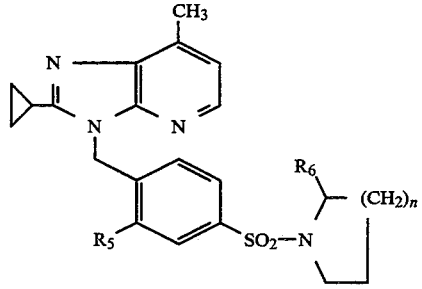

| Ex. No. | R⁵ | R⁶ | n | Configuration | $R_f$* | Yield [%] |
|---|---|---|---|---|---|---|
| 11 | H | —CO₂C(CH₃)₃ | 1 | S | 0.64[a] | 26.5 |
| 12 | Cl | —CO₂C(CH₃)₃ | 1 | S | 0.77[a] | 35.3 |
| 13 | H | —CO₂C(CH₃)₃ | 2 | rac | 0.75[a] | 28.9 |
| 14 | Cl | —CO₂C(CH₃)₃ | 2 | rac | 0.81[a] | 30.2 |
| 15 | H | —CO₂H | 1 | S | 0.26[d] | 99.3 |
| 16 | Cl | —CO₂H | 1 | S | 0.40[d] | 99.5 |
| 17 | H | —CO₂H | 2 | rac | 0.58[d] | 99.6 |
| 18 | Cl | —CO₂H | 2 | rac | 0.68[d] | 99.5 |
| 19 | Cl | —CO₂CH₃ | 1 | S | 0.42[a] | 84.9 |

Example 20

S-4-[[2-Ethyl-imidazo[4,5-b]5,7-dimethyl-pyridin]-3-yl]methyl-3-chloro-benzenesulphonyl-N-(2-methoxycarbonyl)pyrrolidinide

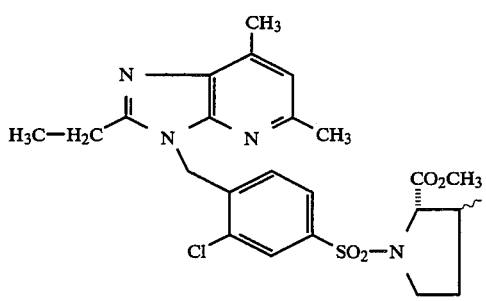

345 mg (2.5 mmol) of potassium carbonate and 99 mg (0.7 mmol) of iodomethane are added in succession to 296 mg (0.5 mmol) of the compound from Example 29 (see Table 4), dissolved in 5 ml of dimethylformamide. The reaction mixture is stirred at 20° C. for a further 10 minutes, and 30 ml of water and 3 ml of 1N HCl are added. The mixture is extracted with ethyl acetate (3×50 ml), the combined organic phases are washed with water (5×50 ml), dried over MgSO₄ and filtered, and all the volatile substances are stripped off in vacuo. 211 mg (86% of theory) of the title compound are obtained.

$R_f$: 0.67 (methylene chloride/methanol 10:1) Configuration: S.

Examples 21 and 22

S-4-[[2-Butyl-imidazo[4,5-b]5,7-dimethyl-pyridin]-3-yl]methyl-3-chloro-benzenesulphonyl-N-(2-carboxy)-pyrrolidinide (Example 21)

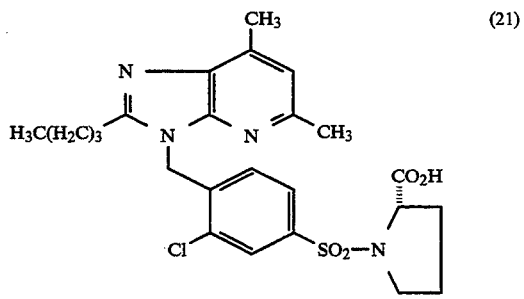
(21)

1.0 g (1.62 mmol) of the compound from Example 47 (see Table 4) is stirred vigorously with 300 ml of buffer solution of pH 7 and 150 ml of chloroform at 20° C. for 0.5 hour. The organic phase is separated off and the aqueous phase is extracted with chloroform (4×50 ml). The combined organic phases are washed with water (2×100 ml), dried over MgSO$_4$ and filtered, and all the volatile substances are stripped off in vacuo. After drying in vacuo, 0.70 g (86% of theory) of the title compound (Example 21) is obtained. Configuration: S.

S-4-[[2-Butyl-imidazo[4,5-b]5,7-dimethyl-pyridin]-3-yl]methyl-3-chloro-benzenesulphonyl-N-(2-carboxy)-pyrrolidinide potassium salt (Example 22)

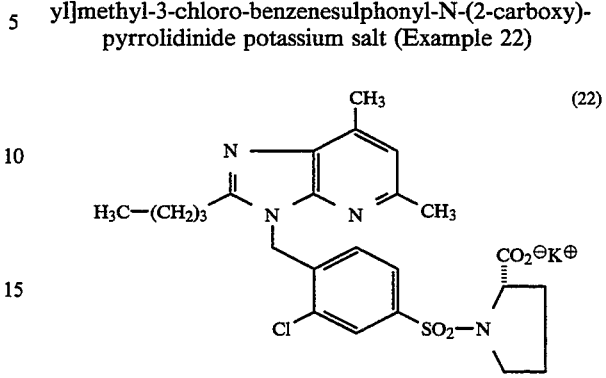
(22)

43 mg (0.66 mol) of 85% pure potassium hydroxide powder are added to 334 mg (0.66 mmol) of the compound from Example 21, dissolved in 5 ml of methanol. The volatile constituents are stripped off in vacuo. After drying, 359 mg (100% of theory) of the title compound in the form of the potassium salt are obtained. (Example 22). Configuration: S.

The compounds in Table 4 are prepared analogously to the instructions of Examples 20, 21 and 22.

TABLE 4

| Ex. No. | $R^1$ | $R^5$ | $R^6$ | n | Configuration | $R_f$ | Yield (% of theory) | Salt |
|---|---|---|---|---|---|---|---|---|
| 23 | △ | Cl | —CO$_2$C(CH$_3$)$_3$ | 1 | S | 0.59$^a$ | 83.0 | |
| 24 | △ | CF$_3$ | —CO$_2$C(CH$_3$)$_3$ | 1 | S | 0.65$^a$ | 83.5 | |
| 25 | △ | Cl | —CO$_2$H | 1 | S | 0.13$^a$ | 100 | TFA*-Salz |
| 26 | △ | CF$_3$ | —CO$_2$H | 1 | S | 0.16$^a$ | 100 | TFA*-Salz |
| 27 | C$_2$H$_5$ | Cl | —CO$_2$C(CH$_3$)$_3$ | 1 | S | 0.69$^a$ | 76.5 | |
| 28 | C$_2$H$_5$ | CF$_3$ | —CO$_2$C(CH$_3$)$_3$ | 1 | S | 0.74$^a$ | 79.5 | |
| 29 | C$_2$H$_5$ | Cl | —CO$_2$H | 1 | S | 0.25$^a$ | 100 | TFA*-Salz |
| 30 | C$_2$H$_5$ | CF$_3$ | —CO$_2$H | 1 | S | 0.28$^a$ | 100 | TFA*-Salz |
| 31 | △ | Cl | —CO$_2$CH$_3$ | 1 | S | 0.57$^a$ | 85.7 | |
| 32 | △ | Cl | —CO$_2$—CH$_2$C$_6$H$_5$ | 1 | S | 0.65$^a$ | 68.5 | |
| 33 | C$_2$H$_5$ | Cl | —CO$_2$—CH$_2$C$_6$H$_5$ | 1 | S | 0.79$^a$ | 59.0 | |
| 34 | △ | F | —CO$_2$C(CH$_3$)$_3$ | 1 | S | 0,69$^a$ | 86.4 | |
| 35 | △ | F | —CO$_2$H | 1 | S | 0,22$^a$ | 100 | TFA*-salt |

TABLE 4-continued

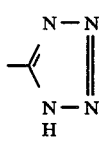

| Ex. No. | R[1] | R[5] | R[6] | n | Configuration | $R_f$ | Yield (% of theory) | Salt |
|---|---|---|---|---|---|---|---|---|
| 36 | △ | F | —CO$_2$CH$_3$ | 1 | S | 0,77[a] | 85.7 | |
| 37 | △ | F | —CO$_2$CH$_2$C$_6$H$_5$ | 1 | S | 0,84[a] | 72.5 | |
| 38 | △ | Cl | —CO$_2$H | 1 | S | | 93.4 | |
| 39 | △ | Cl | —CO$_2$H | 1 | S | | 94.9 | K**-salt |
| 40 | —C$_2$H$_5$ | Cl | —CO$_2$H | 1 | S | | 76.9 | |
| 41 | —C$_2$H$_5$ | Cl | —CO$_2$H | 1 | S | | 96.7 | K**-salt |
| 42 | △ | Cl | —CO$_2$CH$_3$ | 1 | S | | 100 | TFA*-salt |
| 43 | —C$_2$H$_5$ | Cl | —CO$_2$CH$_3$ | 1 | S | | 100 | TFA*-salt |
| 44 | —C$_2$H$_5$ | Cl | —CO$_2$—CH$_2$C$_6$H$_5$ | 1 | S | | 100 | TFA*-salt |
| 45 | △ | Cl | —CO$_2$—CH$_2$C$_6$H$_5$ | 1 | S | | 100 | TFA*-salt |
| 46 | n-C$_4$H$_9$ | Cl | —CO$_2$C(CH$_3$)$_3$ | 1 | S | 0.26[e] | 85.9 | |
| 47 | n-C$_4$H$_9$ | Cl | —CO$_2$H | 1 | S | 0.13[a] | 100 | TFA*-salt |
| 48 | △ | Cl | 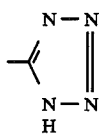 | 1 | S | 0.07[e] | 24.8 | |
| 49 | △ | Cl | 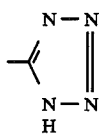 | 1 | S | | 98.8 | |

*TFA = trifluoroacetic acid
**K = potassium

Example 50

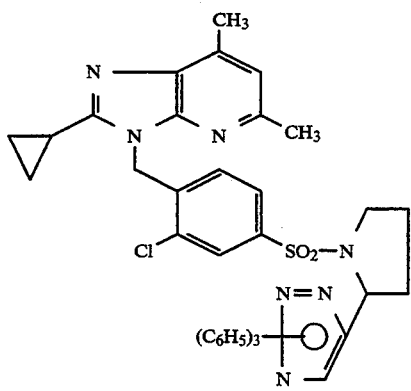

Analogously to the instructions for Example 1, 2.08 g (60% of theory) of the title compound are obtained from 3 g (4.62 mmol) of the compound from Example XIV.

$R_f$=0.46 (petroleum ether/ethyl acetate 1:1).

The compounds in Table 5 are prepared analogously to the instructions of Example 1 and 2:

TABLE 5

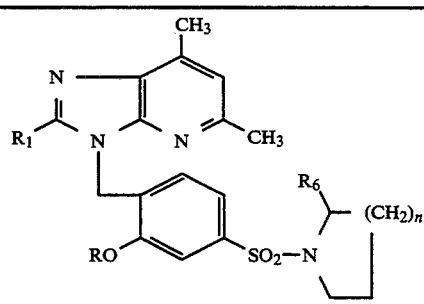

| Example No. | $R^1$ | $R^5$ | $R^6$ | n | Konfig. | $R_f$ | Yield (% of theory) |
|---|---|---|---|---|---|---|---|
| 51 | △ | —O—CH₂—C₆H₅ | —CO₂C(CH₃)₃ | 1 | S | 0,19[g] | 86 |
| 52 | △ | —O—CH₂—C₆H₅ | —CO₂H | 1 | S | 0,17[a] | 98 |
| 53 | △ | —H | —CO₂H | 1 | S | 0,26[f] | 53 |
| 54 | △ | —H | —CO₂C(CH₃)₃ | 1 | S | 0,23[b] | 89 |

We claim:

1. A sulphonylbenzyl-substituted imidazopyridine of the formula

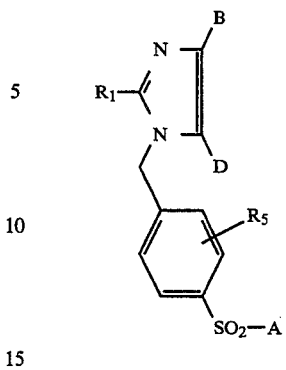

in which
$R^1$ represents straight-chain or branched alkyl or alkenyl having in each case up to 8 carbon atoms, which are optionally substituted by cycloalkyl having 3 to 6 carbon atoms, or represents cycloalkyl having 3 to 8 carbon atoms,
B and D together form a heterocyclic radical of the formula

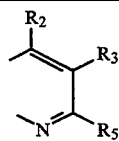

wherein
$R^2$ and $R^3$ are identical or different and denote hydrogen, halogen or straight-chain or branched alkyl having up to 8 carbon atoms,
$R^4$ has the abovementioned meaning of $R^2$ and $R^3$ and is identical to or different from these, or denotes a group of the formula —CO—$R^6$, wherein R$^6$ denotes hydroxyl, straight-chain or branched alkoxy having up to 8 carbon atoms, phenoxy, benzyloxy or a group of the formula —NR$^7$R$^8$, wherein R$^7$ and R$^8$ are identical or different and denote hydrogen or straight-chain or branched alkyl having up to 6 carbon atoms or phenyl, R$^5$ represents hydrogen, halogen or straight-chain or branched alkyl having up to 8 carbon atoms, or represents straight-chain or branched perfluoroalkyl having up to 6 carbon atoms, or represents a group of the formula —OX, wherein X denotes hydrogen, benzyl, a hydroxy protective group or denotes straight-chain or branched alkyl having up to 8 carbon atoms, A represents a 3- to 5 membered saturated heterocyclic radical which is bonded via the nitrogen atom, contains up to 2 further heteroatoms selected from the group consisting of S, N and O and is optionally substituted up to twice, in an identical or different manner, by perfluoroalkyl having up to 5 carbon atoms or by a radical of the formula —SO$_3$H,

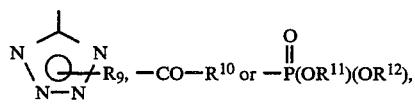

wherein

R$^9$ denotes hydrogen, straight-chain or branched alkyl having up to 6 carbon atoms or triphenylmethyl, R$^{10}$ has the abovementioned meaning of R$^6$ and is identical to or different from this radical and R$^{11}$ and R$^{12}$ are identical or different and denote hydrogen, straight-chain or branched alkyl having up to 8 carbon atoms or phenyl, and salts thereof.

2. A sulphonylbenzyl-substituted imidazolpyridine according to claim 1, wherein

R$^1$ represents straight-chain or branched alkyl or alkenyl having in each case up to 6 carbon atoms, which are optionally substituted by cyclopropyl, cyclobutyl, cyclopentyl or cyclohexyl, or represents cyclopropyl, cyclopentyl or cyclohexyl, R$^2$ and R$^3$ are identical or different and denote hydrogen, fluorine, chlorine, bromine or straight-chain or branched alkyl having up to 6 carbon atoms, R$^4$ has the abovementioned meaning of R$^2$ and R$^3$ and is identical to or different from these radicals, or denotes a group of the formula —CO—R$^6$, wherein R$^6$ denotes hydroxyl, straight-chain or branched alkoxy having up to 6 carbon atoms, phenoxy, benzyloxy or a group of the formula —NR$^7$R$^8$, wherein R$^7$ and R$^8$ are identical or different and denote hydrogen or straight-chain or branched alkyl having up to 4 carbon atoms, R$^5$ represents hydrogen, fluorine, chlorine, bromine or straight-chain or branched alkyl having up to 6 carbon atoms, or represents straight-chain or branched perfluoroalkyl having up to 4 carbon atoms, or represents a group of the formula —OX, wherein X denotes hydrogen, benzyl, acetyl, or denotes straight-chain or branched alkyl having up to 6 carbon atoms, A represents azetidinyl or pyrrolidinyl, which are bonded via the nitrogen atom and are optionally substituted by trifluoromethyl or by a radical of the formula —SO$_3$H,

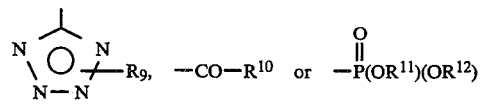

wherein

R$^9$ denotes hydrogen, straight-chain or branched alkyl having up to 4 carbon atoms or triphenylmethyl, R$^{10}$ has the abovementioned meaning of R$^6$ and is identical to or different from this radical and R$^{11}$ and R$^{12}$ are identical or different and denote hydrogen, straight-chain or branched alkyl having up to 6 carbon atoms or phenyl, and salts thereof.

3. A sulphonylbenzyl-substituted imidazopyridine according to claim 1, wherein

R$^1$ represents straight-chain or branched alkyl or alkenyl having in each case up to 4 carbon atoms, or cyclopropyl, R$^2$ and R$^3$ are identical or different and denote hydrogen, fluorine, chlorine, bromine or straight-chain or branched alkyl having up to 4 carbon atoms, R$^4$ has the abovementioned meaning of R$^2$ and R$^3$ and is identical to or different from these radicals, or denotes a group of the formula —CO—R$^6$, wherein R$^6$ denotes hydroxyl, straight-chain or branched alkoxy having up to 4 carbon atoms, phenoxy, benzyloxy or a group of the formula —NR$^7$R$^8$, wherein R$^7$ and R$^8$ are identical or different and denote hydrogen or straight-chain or branched alkyl having up to 3 carbon atoms, R$^5$ represents hydrogen, fluorine, chlorine or straight-chain or branched alkyl having up to 4 carbon atoms, or represents straight-chain or branched perfluoroalkyl having up to 3 carbon atoms, or represents a group of the formula —OX, wherein X denotes hydrogen, benzyl, acetyl or denotes straight-chain or branched alkyl having up to 6 carbon atoms, A represents azetidinyl or pyrrolidinyl, which are bonded via the nitrogen atom and are optionally substituted by trifluoromethyl or by a radical of the formula —SO$_3$H,

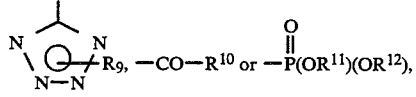

wherein

R⁹ denotes hydrogen, methyl, ethyl or triphenylmethyl,

R¹⁰ has the abovementioned meaning of R⁶ and is identical to or different from this radical and R¹¹ and R¹² are identical or different and denote hydrogen, straight-chain or branched alkyl having up to 4 carbon atoms or phenyl.

4. A compound according to claim 1, wherein such compound is 4-[{2-cyclopropyl-7-methyl-imidazo[4,5-b]pyridin}-3-yl]methyl(3-chlorobenzene)sulphonyl-N-(2-methoxy-carbonyl)-pyrrolidimide of the formula

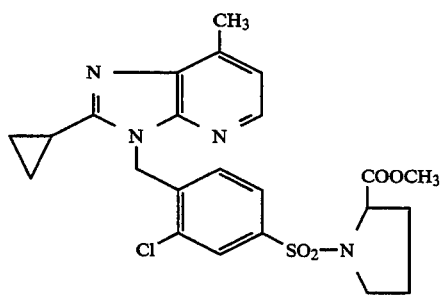

or a salt thereof.

5. A compound according to claim 1, wherein such compound is 5-4-[2-ethyl-imidazo[4,5-b]-5,7-di-methyl-pyridin]-3-yl]methyl(3-chlorobenzene)sulphonyl-N-(2-methoxy-carbonyl)-pyrrolidimide of the formula

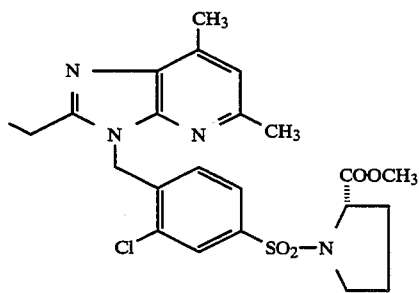

or a salt thereof.

6. A compound according to claim 1, wherein such compound is 4-[[2-cyclopropyl-imidazo[4,5-b]-5,7-dimethyl-pyridin]-3-yl]methyl(3-chlorobenzene)sulphonyl-N-(2-methoxy-carbonyl)-pyrrolidimide of the formula

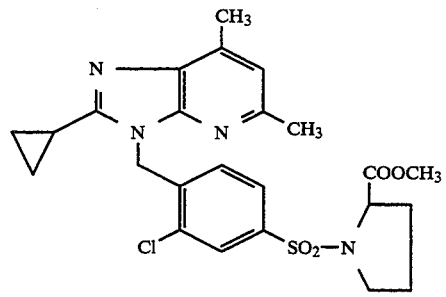

or a salt thereof.

7. A compound according to claim 1, wherein such compound is 4-[[2-cyclopropyl-imidazo[4,5-b]-5,7-dimethyl-pyridin]-3-yl]methyl(3-chlorobenzene)sulphonyl-N-(2-carboxy)-pyrrolidimide of the formula

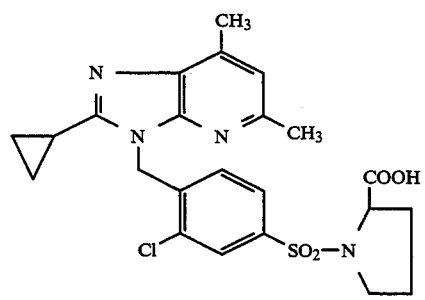

or a salt thereof.

8. A compound according to claim 1, wherein such compound is 4-[[2-ethyl-imidazo[4,5-b]-5,7-dimethyl-pyridin]-3-yl]methyl(3-chlorobenzene)sulphonyl-N-(2-carboxy)-pyrrolidimide of the formula

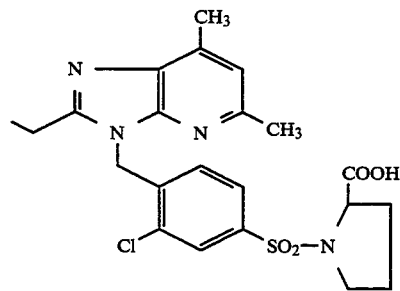

or a salt thereof.

9. A composition for the treatment of atriable hypertension comprising an amount effective therefor of a compound or salt thereof according to claim 1 and a pharmaceutically acceptable diluent.

10. The method of treating atriable hypertension in a patient in need thereof which comprises administering to such patient an amount effective therefor of a compound and salt thereof according to claim 1.

* * * * *

UNITED STATES PATENT AND TRADEMARK OFFICE
CERTIFICATE OF CORRECTION

PATENT NO. : 5,364,942
DATED : November 15, 1994
INVENTOR(S) : Hanko, et al.

It is certified that error appears in the above-indentified patent and that said Letters Patent is hereby corrected as shown below:

Col. 30, line 59  Delete " 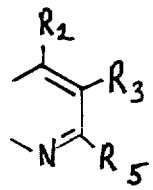 " and substitute

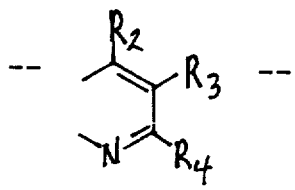

Col. 31, line 15  Delete " hydroxy " and substitute -- hydroxyl --

Signed and Sealed this

Twenty-sixth Day of September, 1995

Attest:

BRUCE LEHMAN

Attesting Officer    Commissioner of Patents and Trademarks